(12) United States Patent
Stec et al.

(10) Patent No.: US 10,940,184 B2
(45) Date of Patent: Mar. 9, 2021

(54) TISSUE MATRIX MATERIALS AND ENZYMATIC ADHESIVES

(71) Applicant: LifeCell Corporation, Branchburg, NJ (US)

(72) Inventors: Eric Stec, Washington, NJ (US); Ming F. Pomerleau, Califon, NJ (US); Rick T. Owens, Stewartsville, NJ (US); Richard Seeman, South Bound Brook, NJ (US)

(73) Assignee: LifeCell Corporation, Madison, NJ (US)

( * ) Notice: Subject to any disclaimer, the term of this patent is extended or adjusted under 35 U.S.C. 154(b) by 344 days.

(21) Appl. No.: 15/882,374

(22) Filed: Jan. 29, 2018

(65) Prior Publication Data

US 2018/0214520 A1 Aug. 2, 2018

Related U.S. Application Data (60) Provisional application No. 62/452,014, filed on Jan. 30, 2017.

(51) Int. Cl.
*A61K 38/39* (2006.01)
*A61L 27/36* (2006.01)
(Continued)

(52) U.S. Cl.
CPC ............ *A61K 38/39* (2013.01); *A01N 1/0226* (2013.01); *A01N 1/0231* (2013.01); *A61K 35/18* (2013.01);
(Continued)

(58) Field of Classification Search
CPC . A61K 38/39; A61L 27/3687; A61L 27/3604; A61L 27/34; A61L 27/3625;
(Continued)

(56) References Cited

U.S. PATENT DOCUMENTS

| | | |
|---|---|---|
| 4,098,571 A | 7/1978 | Miyata et al. |
| 5,336,616 A | 8/1994 | Livesey et al. |

(Continued)

FOREIGN PATENT DOCUMENTS

| | | |
|---|---|---|
| GB | 2482166 A | 1/2012 |
| JP | 2002-507907 A | 3/2002 |

(Continued)

OTHER PUBLICATIONS

Stachel et al., Cross-linking of type I collagen with microbial transglutaminase: identification of cross-linking sites. Biomacromolecules, vol. 11, No. 3 (2011) pp. 698-705. (Year: 2011).*

(Continued)

*Primary Examiner* — Kara D Johnson
(74) *Attorney, Agent, or Firm* — McCarter & English, LLP

(57) ABSTRACT

The present application relates to use of transglutaminases to treat various tissue matrix products. The methods can include application of a transglutaminase to a partially denatured collagen-containing tissue matrix and implantation of the tissue matrix. The transglutaminase can facilitate adhesion with another collagen-containing tissue matrix, tissue surrounding the tissue matrix after implantation, or both.

17 Claims, 5 Drawing Sheets

(51) Int. Cl.
*A61L 27/34* (2006.01)
*A61L 24/10* (2006.01)
*A01N 1/02* (2006.01)
*A61K 35/18* (2015.01)
*A61K 48/00* (2006.01)
*C12N 9/10* (2006.01)
*A61L 27/24* (2006.01)

(52) U.S. Cl.
CPC ............ *A61K 48/00* (2013.01); *A61L 24/102* (2013.01); *A61L 27/24* (2013.01); *A61L 27/34* (2013.01); *A61L 27/3604* (2013.01); *A61L 27/367* (2013.01); *A61L 27/3625* (2013.01); *A61L 27/3687* (2013.01); *A61L 27/3695* (2013.01); *C12N 9/1048* (2013.01); *A61L 2430/40* (2013.01)

(58) Field of Classification Search
CPC .. A61L 27/367; A61L 2430/40; A01N 1/0231
See application file for complete search history.

(56) References Cited

U.S. PATENT DOCUMENTS

| | | | |
|---|---|---|---|
| 5,364,756 | A | 11/1994 | Livesey et al. |
| 5,855,620 | A | 1/1999 | Bishopric et al. |
| 6,166,288 | A | 12/2000 | Diamond et al. |
| 6,267,786 | B1 | 7/2001 | Stone |
| 6,379,710 | B1 | 4/2002 | Badylak |
| 6,455,309 | B2 | 9/2002 | Stone |
| 6,835,385 | B2 | 12/2004 | Buck |
| 7,498,412 | B2 | 3/2009 | Huang et al. |
| 8,961,544 | B2 | 2/2015 | Komlos et al. |
| 9,206,442 | B2 | 12/2015 | Chen |
| 9,238,793 | B2 | 1/2016 | Chen et al. |
| 9,259,511 | B2 | 2/2016 | Sun |
| 9,956,316 | B2 | 5/2018 | Chen |
| 9,957,477 | B2 | 5/2018 | Chen et al. |
| 10,022,473 | B2 | 7/2018 | Sun |
| 2002/0115208 | A1 | 8/2002 | Mitchell et al. |
| 2003/0035843 | A1 | 2/2003 | Livesey et al. |
| 2003/0068815 | A1 | 4/2003 | Stone et al. |
| 2003/0143207 | A1 | 7/2003 | Livesey et al. |
| 2004/0191226 | A1 | 9/2004 | Badylak |
| 2004/0234507 | A1 | 11/2004 | Stone |
| 2004/0243250 | A1 | 12/2004 | Stone et al. |
| 2005/0028228 | A1 | 2/2005 | McQuillan et al. |
| 2005/0186286 | A1 | 8/2005 | Takami |
| 2005/0260176 | A1 | 11/2005 | Ayares et al. |
| 2006/0073592 | A1 | 4/2006 | Sun et al. |
| 2006/0127375 | A1 | 6/2006 | Livesey et al. |
| 2006/0210960 | A1 | 9/2006 | Livesey et al. |
| 2006/0272102 | A1 | 12/2006 | Liu et al. |
| 2007/0009586 | A1 | 1/2007 | Cohen et al. |
| 2007/0010897 | A1 | 1/2007 | Stone |
| 2007/0248575 | A1 | 10/2007 | Connor et al. |
| 2008/0027562 | A1 | 1/2008 | Fujisato et al. |
| 2009/0202977 | A1 | 8/2009 | Ott et al. |
| 2009/0239809 | A1 | 9/2009 | Chen et al. |
| 2009/0306790 | A1 | 12/2009 | Sun |
| 2010/0119577 | A1 | 5/2010 | Min et al. |
| 2010/0179639 | A1 | 7/2010 | Bloor et al. |
| 2010/0196870 | A1 | 8/2010 | Stone et al. |
| 2010/0233235 | A1 | 9/2010 | Matheny et al. |
| 2011/0021753 | A1 | 1/2011 | Huang |
| 2012/0252065 | A1 | 10/2012 | Rozenszain et al. |
| 2012/0276213 | A1 | 11/2012 | Chen |
| 2013/0028981 | A1 | 1/2013 | Gratzer |
| 2014/0377833 | A1 | 12/2014 | Chen et al. |
| 2015/0282925 | A1* | 10/2015 | Xu .................. A61L 27/362 623/14.13 |
| 2016/0045639 | A1 | 2/2016 | Chen |
| 2016/0090572 | A1 | 3/2016 | Chen et al. |
| 2016/0114080 | A1 | 4/2016 | Sun |

FOREIGN PATENT DOCUMENTS

| | | |
|---|---|---|
| JP | 2004-107303 A | 4/2004 |
| WO | 1994/28949 A1 | 12/1994 |
| WO | 2001/091671 A1 | 12/2001 |
| WO | 2004/020470 A1 | 3/2004 |
| WO | 2006/095342 A2 | 9/2006 |
| WO | 2008/125850 A2 | 10/2008 |
| WO | 2009/049568 A2 | 4/2009 |
| WO | 2009/133532 A1 | 11/2009 |
| WO | 2010/002799 A2 | 1/2010 |
| WO | WO-2010002799 A2 * | 1/2010 ............ A61L 27/50 |

OTHER PUBLICATIONS

Collighan et al., Transglutaminase 2 cross-linking of matrix proteins: biological significance and medical applications. Amino Acids. Apr. 2009;36(4):659-70.

Stachel et al., Cross-linking of type I collagen with microbial transglutaminase: identification of cross-linking sites. Biomacromolecules. Mar. 8, 2010;11(3):698-705.

Wang et al., Comparison between Thermal Hydrolysis and Enzymatic Proteolysis Processes for the Preparation of Tilapia Skin Collagen Hydrolysates. Czech J Food Sci. 2013;31(1):1-4.

International Search Report and Written Opinion for Application No. PCT/US2018/015685, dated Apr. 19, 2018. 16 pages.

Badylak et al., Extracellular matrix as a biological scaffold material: Structure and function. Acta Biomater. Jan. 2009;5(1):1-13.

Dobrin et al., Elastase, collagenase, and the biaxial elastic properties of dog carotid artery. Am J Physiol. Jul. 1984;247(1 Pt 2):H124-31.

Gilbert et al., Decellularization of tissues and organs. Biomaterials. Jul. 2006;27(19):3675-83.

Ionescu et al., Effect of Papain and Bromelin on Muscle and Collagen Proteins in Beef Meat. The Annals of the University Dunarea de Jos of Galati. Fascicle VI, Food Technology, New Series, pp. 9-16, 2008.

Karlinsky et al., In vitro effects of elastase and collagenase on mechanical properties of hamster lungs. Chest. Feb. 1976;69(2 Suppl):275-6.

Lu et al., Novel porous aortic elastin and collagen scaffolds for tissue engineering. Biomaterials. Oct. 2004;25(22):5227-37.

Parenteau-Bareil et al., Collagen-Based Biomaterials for Tissuse Engineering Applications. Materials. 2010;3:1863-1887.

Reihsner et al., Biomechanical properties of elastase treated palmar aponeuroses. Connect Tissue Res. 1991;26(1-2):77-86.

Tedder et al., Stabilized collagen scaffolds for heart valve tissue engineering. Tissue Eng Part A. Jun. 2009;15(6):1257-68.

Yuan et al., Effects of collagenase and elastase on the mechanical properties of lung tissue strips. J Appl Physiol(1985). Jul. 2000;89(1):3-14.

* cited by examiner

TISSUE MATRIX MATERIALS AND ENZYMATIC ADHESIVES

This application claims priority under 35 U.S.C. § 119 to U.S. Provisional Application No. 62/452,014, filed Jan. 30, 2017, the entire contents of which is incorporated herein by reference.

The present disclosure relates to tissue products, including methods of using and processing tissue products using transglutaminases.

Various tissue-derived products are used to regenerate, repair, or otherwise treat diseased or damaged tissues and organs. Such products can include intact tissue grafts or acellular or reconstituted acellular tissues (e.g., acellular tissue matrices from skin, intestine, or other tissues, with or without cell seeding). Such products can also include hybrid or composite materials, e.g., materials including synthetic components such as a polymeric mesh substrate with a coating or covering that includes materials derived from tissue.

In some cases, it may be desirable to join collagen-containing tissue matrix products to one another or to tissues within the body. There are currently a variety of ways to join such materials or tissues, including, for example, adhesives, mechanical fixation systems (e.g., sutures), or chemical modifications. Current devices and methods, however, may not be ideal for some applications.

For example, some surgical adhesives, although suitable for superficial use, are not recommended for implantation deep in the body. In addition, mechanical fixation mechanisms can be time consuming to use and may leave gaps between tissue planes, which may be undesirable as such gaps can lead to complications such as seroma formation. Furthermore, adhesives or other chemical joining mechanisms can produce undesirable changes in regenerative tissue matrices or can themselves create barrier layers that prevent desired cellular ingrowth and vascularization, and some adhesives may generate toxic byproducts unsuitable for implantation.

Accordingly, the present disclosure provides improved methods for joining collagen-containing tissue products to one another or to tissues.

SUMMARY

According to one embodiment, a method of producing a tissue product is provided. The method can include selecting a first material comprising a collagen-containing tissue matrix; treating a portion of the first material to partially denature collagen near a surface of the portion of the first material; contacting the portion that has been treated to partially denature collagen with a composition comprising a transglutaminase enzyme; and placing the portion that has been contacted with the composition comprising transglutaminase in physical contact with a second material comprising a collagen-containing tissue matrix.

According to one embodiment, a method of treatment is provided. The method can include selecting a material comprising a collagen-containing tissue matrix; treating a portion of the material to partially denature collagen near a surface of the portion; contacting the portion that has been treated to partially denature collagen with a composition comprising a transglutaminase enzyme; and placing the portion that has been contacted with the composition comprising transglutaminase in physical contact with a tissue site.

According to another embodiment, a tissue treatment product is provided. The product can include a first material comprising a collagen-containing acellular tissue matrix; and at least one second material comprising a collagen-containing acellular tissue matrix, wherein the first material and second material are joined to one another by bonds formed between gamma-carboxamide groups of glutamine residues with primary amino acids.

According to another embodiment, a method of treatment is provided. The method can include selecting a material comprising a collagen-containing tissue matrix. A portion of the material proximate a surface of the material includes partially denatured collagen. The method can include contacting the portion including partially denatured collagen with a composition comprising a transglutaminase enzyme. The method can include placing the portion that has been contacted with the composition comprising transglutaminase in physical contact with a tissue site.

According to another embodiment, a tissue treatment product is provided. The product can include an acellular tissue matrix having a substantially intact acellular collagen tissue matrix, and a surface region comprising partially denatured collagen, wherein the partially denatured collagen comprises collagen matrix formed from the same tissue as the substantially intact acellular collagen tissue matrix such that the partially denatured collagen is formed from the native collagen framework of the intact tissue matrix and is connected to the intact tissue matrix.

According to one embodiment, a method of producing a tissue product is provided. The method can include selecting a first material comprising a collagen-containing tissue matrix and treating a portion of the first material to partially denature collagen near a surface of the portion of the first material thereby forming a portion of partially denatured collagen that is connected to the collagen-containing tissue matrix.

DESCRIPTION OF CERTAIN EXEMPLARY EMBODIMENTS

Reference will now be made in detail to certain exemplary embodiments according to the present disclosure, certain examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Any range described herein will be understood to include the endpoints and all values between the endpoints.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

Various human and animal tissues can be used to produce products for treating patients. For example, various tissue products for regeneration, repair, augmentation, reinforcement, and/or treatment of human tissues that have been damaged or lost due to various diseases and/or structural damage (e.g., from trauma, surgery, atrophy, and/or long-term wear and degeneration) have been produced. Such products can include, for example, acellular tissue matrices, tissue allografts or xenografts, and/or reconstituted tissues (i.e., at least partially decellularized tissues that have been seeded with cells to produce viable materials).

Tissue products can be selected to provide a variety of different biological and mechanical properties. For example, an acellular tissue matrix or other tissue product can be selected to allow tissue ingrowth and remodeling to assist in regeneration of tissue normally found at the site where the matrix is implanted. For example, an acellular tissue matrix, when implanted on or into fascia, may be selected to allow regeneration of the fascia without excessive fibrosis or scar formation. In certain embodiments, the tissue product can be formed from ALLODERM® or STRATTICE™, which are human and porcine acellular dermal matrices, respectively. Alternatively, other suitable acellular tissue matrices are available. For example, a number of biological scaffold materials are described by Badylak et al., "Extracellular Matrix as a Biological Scaffold Material: Structure and Function," *Acta Biomaterialia* (2008), doi:10.1016/j.actbio.2008.09.013.

As used herein "tissue product" will refer to any human or animal tissue that contains an extracellular matrix protein. "Tissue products" can include acellular or partially decellularized tissue matrices, decellularized tissue matrices that have been repopulated with exogenous cells, and/or cellular tissues. The "tissue products" can be in a variety of shapes or forms, e.g., as flexible sheets, as particulate or cut/shaped pieces, or as bulk masses (e.g., box, ovoid, spherical, or irregular 3-D shapes). The tissue products can include hybrid products that include two or more different tissue types, for example, a tissue matrix from dermis and muscle, dermis and fascia, muscle and fascia, or dermis and adipose tissue, or other combinations.

The term "acellular tissue matrix," (e.g., ATM) as used herein, refers generally to any tissue matrix that is substantially free of cells and/or cellular components. Skin, parts of skin (e.g., dermis), and other tissues such as adipose, blood vessels, heart valves, fascia, cartilage, bone, muscle (skeletal or non-skeletal) and nerve connective tissue may be used to create acellular matrices within the scope of the present disclosure. Acellular tissue matrices can be tested or evaluated to determine if they are substantially free of cell and/or cellular components in a number of ways. For example, processed tissues can be inspected with light microscopy to determine if cells (live or dead) and/or cellular components remain. In addition, certain assays can be used to identify the presence of cells or cellular components.

Transglutaminases are enzymes expressed in bacteria, plants, and animals that catalyze the binding of gamma-carboxamide groups of glutamine residues with amino groups of lysine residues or other primary amino groups. Transglutaminases are used in the food industry for binding and improving the physical properties of protein rich foods such as meat, yogurt, and tofu. Transglutaminases are also currently being explored for use in the medical device industry as hydrogels and sealants. See Aberle, T. et al., "Cell-type Specific Four Component Hydrogel," PLoS ONE 9(1): e86740 (January 2004).

The present inventors have recognized that transglutaminases may be used to catalyze binding of two or more collagen-containing materials to one another. The two or more collagen-containing materials can include "tissue products," as discussed above, including acellular tissue matrices, or can include a tissue product and tissue found in a patient (e.g., fascia or other tissue surrounding an implant site in the abdominal wall, breast, or other tissue sites).

Although transglutaminases have some enzymatic effect on collagen-containing materials, the present inventors have also discovered that the use of transglutaminases to bind or join two or more materials can be improved by causing partial denaturation of collagen at or near the surface of the tissues, thereby making amine and acyl groups of collagen amino acids more accessible for enzymatic crosslinking. By partially denaturing collagen contained at or near the surface of the material, the denatured collagen will remain connected to the fibrillar collagen network of the tissue product, and exogenous gelatin will not be needed to assist in binding with other materials such as other tissue products or tissue at an implantation site.

According to one embodiment, a method of producing a tissue product is provided. The method can include selecting a first material comprising a collagen-containing tissue matrix; treating a portion of the first material to partially denature collagen near a surface of the portion; contacting the portion that has been treated to partially denature collagen with a composition comprising a transglutaminase enzyme; and placing the portion that has been contacted with the composition comprising transglutaminase in physical contact with a second material comprising a collagen-containing tissue matrix.

According to another embodiment, a tissue treatment product is provided. The product can include an acellular tissue matrix having a substantially intact acellular collagen tissue matrix, and a surface region comprising partially denatured collagen, wherein the partially denatured collagen comprises collagen matrix formed from the same tissue as the substantially intact acellular collagen tissue matrix such that the partially denatured collagen is formed from the native collagen framework and is connected to the intact tissue matrix.

According to another embodiment, a method of treatment is provided. The method can include selecting a material comprising a collagen-containing tissue matrix; treating a portion of the material to partially denature collagen near a surface of the portion; contacting the portion that has been treated to partially denature collagen with a composition comprising a transglutaminase enzyme; and placing the portion that has been contacted with the composition comprising transglutaminase in physical contact with a tissue site.

According to another embodiment, a tissue treatment product is provided. The product can include a first material comprising a collagen-containing acellular tissue matrix; and at least one second material comprising a collagen-containing acellular tissue matrix, wherein the first material and second material are joined to one another by bonds formed between gamma-carboxamide groups of glutamine residues with primary amino acids.

According to one embodiment, a method of producing a tissue product is provided. The method can include selecting a first material comprising a collagen-containing tissue matrix and treating a portion of the first material to partially denature collagen near a surface of the portion of the first material thereby forming a portion of partially denatured collagen that is connected to the collagen-containing tissue matrix.

Figure 1:
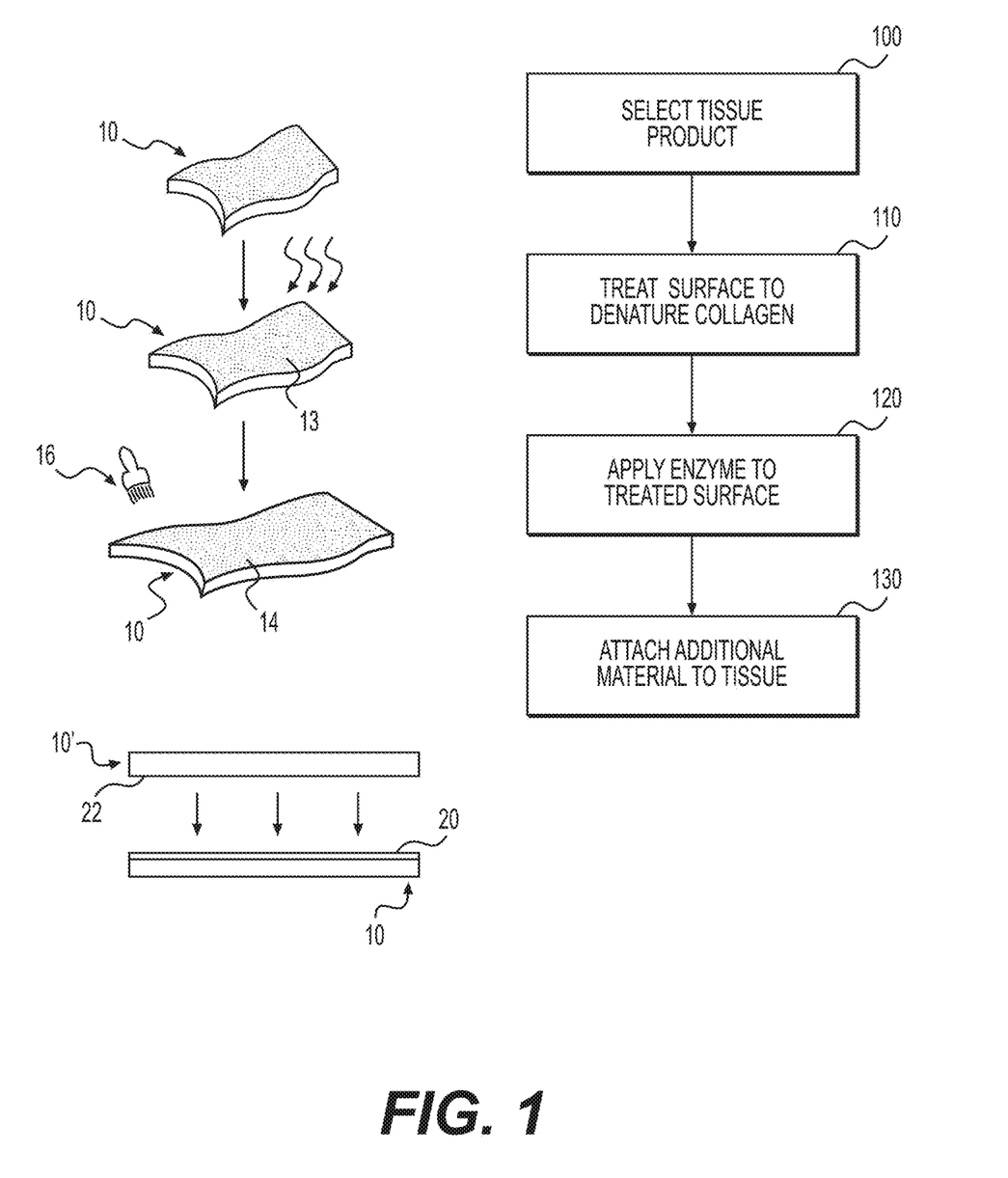
FIG. 1 illustrates a process for joining tissue products using transglutaminases, according to various embodiments.
Figure 2:
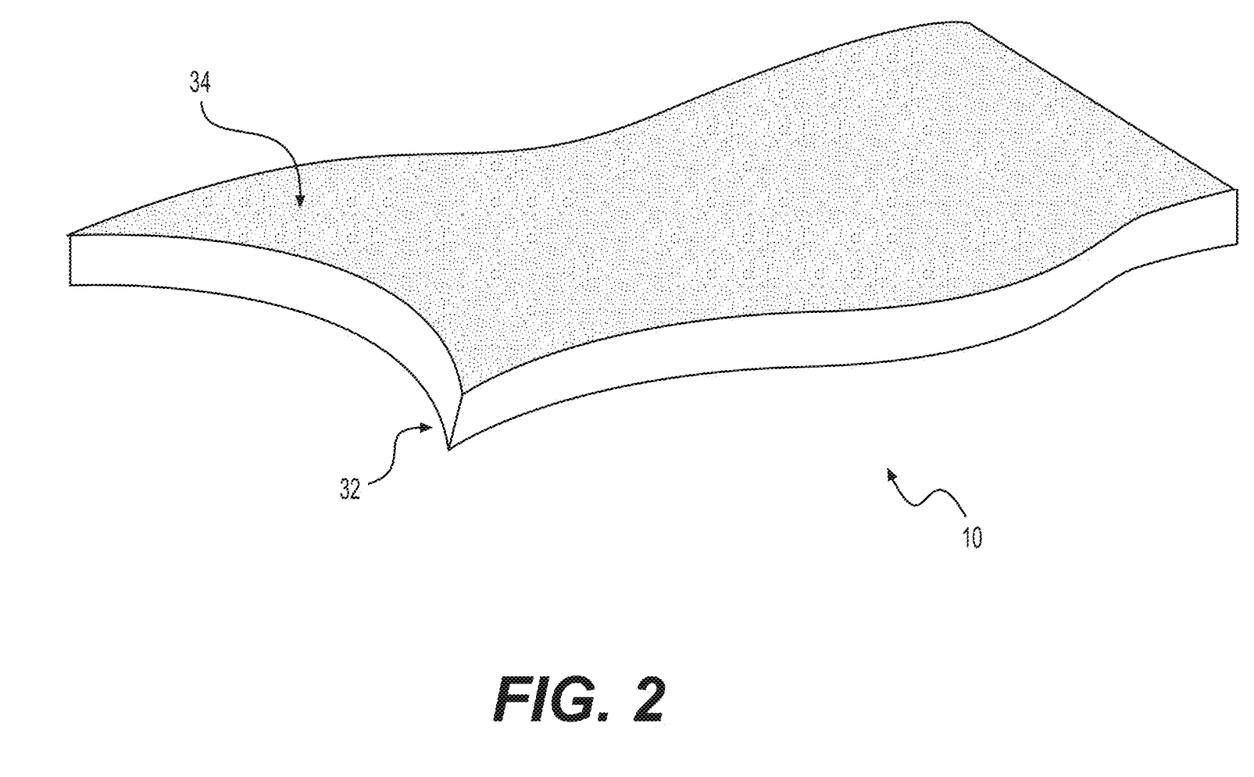
FIG. 2 is a perspective view of a sheet tissue product that may be treated using the disclosed processes.
Figure 3:
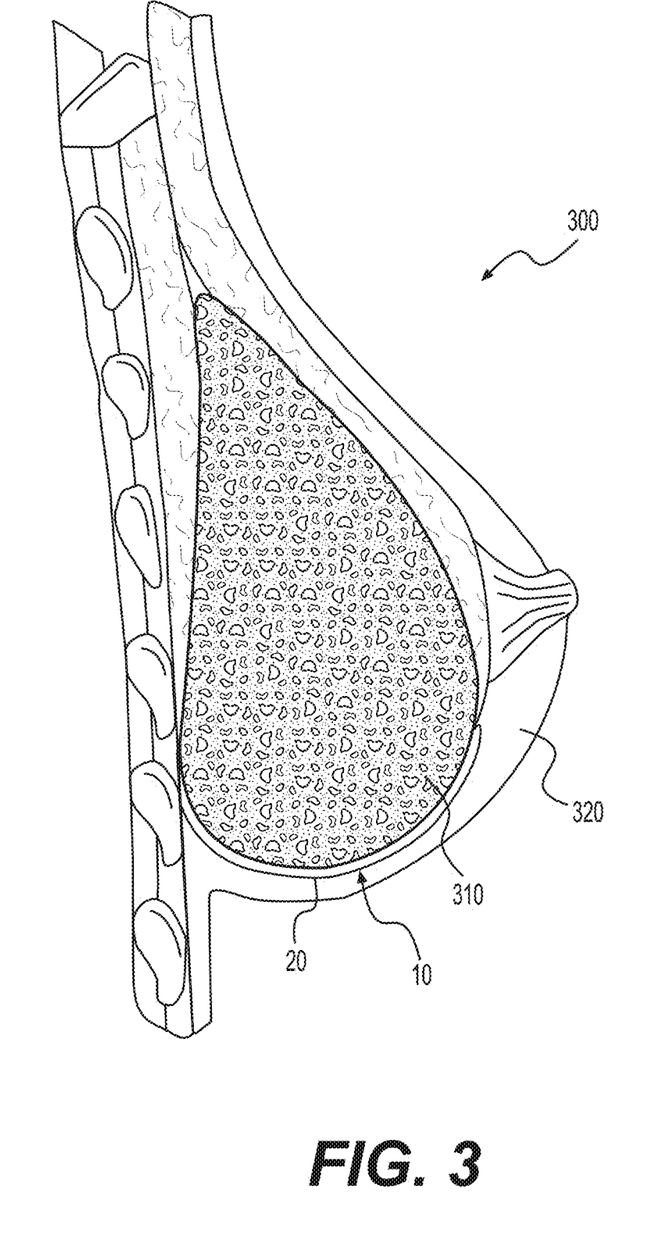
FIG. 3 is a side view of a tissue product implanted along with a breast implant or tissue expander and incorporating transglutaminases to bind the tissue product to surrounding tissues, according to various embodiments.
Figure 4:
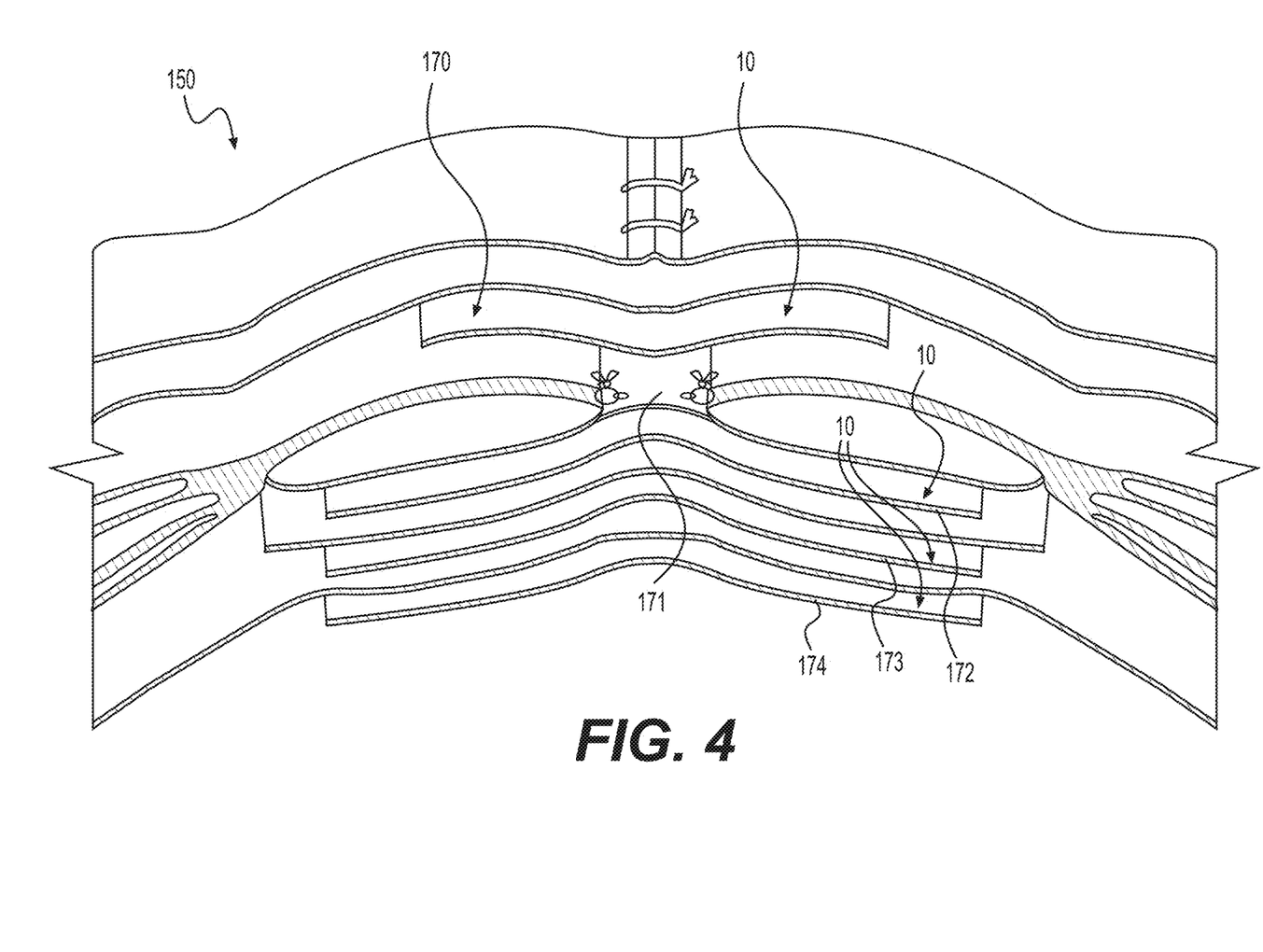
FIG. 4 illustrates use of sheet tissue products to treat abdominal sites in which the disclosed transglutaminase treatment methods may be incorporated.

A more detailed explanation of the methods and products described above is now provided. FIG. 1 illustrates a process for joining tissue products using transglutaminases, according to various embodiments. FIG. 2 is a perspective view of a sheet tissue product that may be treated using the disclosed processes. And FIG. 3 is a side view of a tissue product implanted with a breast implant or tissue expander and incorporating transglutaminases to bind the tissue product to surrounding tissues, according to various embodiments, while FIG. 4 illustrates use of sheet tissue products to treat abdominal sites in which the disclosed transglutaminase treatment methods may be incorporated.

FIG. 1 provides a general scheme for implementing the methods of joining tissue products to one another or for joining tissue products with tissues in vivo. As shown, the process starts with selection of the desired tissue product(s) 10 (Step 100). As discussed above, the tissue products can include any of a variety of different collagen-containing materials, including, for example, acellular or partially decellularized tissue matrices, decellularized tissue matrices that have been repopulated with exogenous cells, and/or cellular tissues.

The tissue product can include a tissue selected from skin, fascia, adipose, pericardial tissue, dura, umbilical cord tissue, placental tissue, cardiac valve tissue, ligament tissue, tendon tissue, arterial tissue, venous tissue, neural connective tissue, urinary bladder tissue, ureter tissue, muscle, and intestinal tissue. In some cases, the tissue product is produced from tissue derived from skin and may comprise dermal tissue matrix with or without accompanying epidermis. In some cases, the tissue product is produced from muscle and may comprise muscle tissue matrix comprising skeletal or non-skeletal tissue.

The tissue product, in addition or alternatively to using an intact acellular tissue matrix sheet or other form, can include tissue matrix that is processed and reformed into a sponge or similar material incorporating particulate or reconstituted tissue matrix. For example, a tissue matrix sponge can be formed by cutting, grinding, or chopping tissue matrix to produce particles or fragments. The particles or fragments can then be formed into a slurry by addition of water, and cast in a container (e.g., as a sheet or other shape), or applied to a substrate before drying (e.g., by air or freeze drying). In some embodiments, optional stabilization steps to cross-link or otherwise stabilize that material can be performed. Exemplary tissue products including a sponge or coating for use with or without a polymeric substrate, are disclosed in U.S. Pat. No. 9,382,422, which issued on Jul. 5, 2016 to LifeCell Corporation.

In some embodiments, a tissue matrix sponge is formed from adipose tissue. Suitable adipose tissues are described generally in US Patent Publication Number 2012/0310367 A1 (U.S. patent application Ser. No. 13/483,674, filed May 30, 2012 by Connor). Such adipose materials can be formed generally by mechanical homogenization, washing, resuspension, and stabilization of the material. The material may be dried (e.g., by freeze drying before or after stabilization). The stabilization can further be used to bond or attach the sponge to the other material. Sterilization may be performed after the components of the devices described herein are joined. Further, the sponge may be formed while in contact with the intact acellular tissue matrix components or may be formed separately prior to joining.

In some embodiments, a multilayered tissue product is formed from muscle tissue matrix. The muscle tissue may be selected from smooth muscle, cardiac muscle, skeletal muscle, or a combination thereof. Each layer of muscle tissue matrix may be joined by treatment with transglutaminase. The multilayered tissue product can include a layer of acellular muscle tissue matrix and at least one layer of additional acellular tissue matrix derived from any natural tissue.

Next, after selection of the tissue product, a portion of the tissue product at or near the surface can be treated to denature or partially denature collagen (Step 110). For example, as shown in FIG. 1, a surface 13 of a flat sheet can be treated to denature collagen. And although treatment of the entire surface 13 of one side of the sheet is illustrated, it should be appreciated that, depending on the intended use, the entire surface or focal areas of the surface (e.g., specific spots, shapes, or areas) can be treated.

The denaturation process can be performed in a number of ways. Methods for controlled denaturation of the tissue matrix collagen may include physical or mechanical processes (e.g., abrasion), thermal processes, chemical processes (e.g., acid, base or other protein denaturants), enzymatic denaturation, application of light (e.g., laser to heat or impart energy), or combinations thereof.

In some cases, after denaturation, the product can be packaged for storage until later use. As such, the product includes a packaged tissue matrix having undergone partial denaturation, and which can be used by surgeons, who may complete application of subsequent steps, including application of transglutaminases prior to or concurrently with implantation.

After denaturation, a transglutaminase composition 16 can be applied to the portion of the tissue 14 that has been treated (Step 120), thereby forming a region 20 containing denaturized collagen and transglutaminase.

The transglutaminase composition can be produced in a number of ways. For example, the transglutaminase can be provided in a solution or formed into a solution from a stored form (e.g., a dry powder or other suitable storage form). The solution can include any suitable buffer such as phosphate buffered saline or other biologically compatible buffer material that will maintain or support enzymatic activity and will not damage the enzyme or tissue product.

Furthermore, a variety of transglutaminases can be used including any that are biologically compatible, can be implanted in a patient, and having sufficient activity to provide desired catalytic results within a desired time frame. Transglutaminases are known and can include microbial, plant, animal, or recombinantly produced enzymes. Depending on the specific enzyme used, modifications such as addition of cofactors, control of pH, or control of temperature or other environmental conditions may be needed to allow appropriate enzymatic activity. Microbial transglutaminases can be effective because they may not require the presence of metal ions, but any suitable transglutaminase may be used.

The enzymatic composition can be applied to the surface of the tissue products using any suitable mechanical means. For example, the composition can be applied by simple brushing (e.g., using a mechanical applicator 16), spraying, dipping, rolling, or any other suitable process.

After the transglutaminase is applied, the collagen-containing tissue matrix that has been treated to include partial denaturation and transglutaminase application can be contacted with one or more additional collagen-containing tissue products 10' or tissues (Step 130). For example, as shown in FIG. 1, the tissue product 10, including the treated portion 20, can be contacted with the surface 22 of another tissue product, thereby bringing the transglutaminase in contact with the other tissue product 10' or tissues.

Although the process shown in FIG. 1 includes denaturation and transglutaminase application to surfaces of certain tissues, equivalent variations may be made. For example, in some cases, the partial denaturation and/or transglutaminase application can be separated or duplicated. For example, in one case, the enzyme is applied to one surface 22, while the partial denaturation process is applied to the other surface 20. Or both surfaces 20, 22 are subject to partial denaturation and transglutaminase application; or both surfaces 20, 22 are subject to partial denaturation, while the transglutaminase is applied directly to only one surface.

As noted above, the tissue product can include a variety of shapes, forms, and tissues. For example, as shown in FIGS. 1 and 2, the tissue product 10 can include a sheet of flexible soft tissue or acellular tissue matrix having at least one surface 20 that is treated, as discussed. In some cases, multiple (two or more) sheets 10 of the tissue products can be joined to form a multi-layer sheet. The sheets can comprise, for example, acellular dermal tissue matrix, acellular muscle tissue matrix, or combinations of different types of tissue matrix products (e.g., acellular dermal matrix laminated with or joined to skeletal muscle matrix, adipose matrix, or other tissues).

As discussed above, the denatured collagen can be formed such that it is integrally connected with the tissue matrix. That is, the partially denatured collagen comprises collagen matrix formed from the same tissue as the substantially intact acellular collagen tissue matrix such that the partially denatured collagen is formed from the native collagen framework and is connected to the intact tissue matrix. So, for example, as shown in FIG. 2, the tissue product 10 can be formed of a single sheet of acellular matrix that has a top surface 34 and a bottom surface 32. In some embodiments, the tissue matrix 30 can be treated to denature a portion of collagen near one or more surfaces 32, 34. The treatment can include any surface, such as a side surface (not numbered), or any desirable surface portion (e.g., for an irregularly shaped material or a material having a shape other than for a flat sheet).

As noted above, rather than, or in addition to, joining two or more tissue products to one another, the present methods can be used to attach tissue products to tissue, e.g., in vivo. Use of the present methods for binding of the tissue treatment products to tissues can provide a number of possible advantages. For example, in some cases, providing secure attachment of tissue products (e.g., sheets of tissue or tissue matrix) to surrounding tissue, can help prevent complications such as seroma, or can help secure the tissue product in place if migration or movement is a concern.

The devices and methods presented herein can therefore be used at a variety of anatomic sites including within or near the breast (e.g., for augmentation, reconstruction, or aesthetic procedures), the abdominal wall (for hernia treatment, to reinforce incisions (e.g., midline, around stomas), etc.), other connective tissue sites (tendon, ligament, fascia), intracranially (for dura replacement), or in any other location where acellular tissue matrices or similar products are desired.

FIGS. 3 and 4 illustrate locations, by example only, where the tissue products of the present disclosure may be used. For example, FIG. 3 illustrates implantation of a tissue product 10 in a breast 300. The product is implanted near a breast implant 310 or tissue expander. Importantly, the surface 20 having collagen that is partially denatured and treated with collagenase is placed in contact with subcutaneous tissues or other surrounding tissue (under the breast skin 320 and facing away from the implant 310). As such, the product 10 will be bound or adhere to surrounding tissue, securing the product 10 in place and/or preventing space from forming.

FIG. 4 provides an illustration of various locations where the tissue matrix 10 can be used within an abdominal wall 150, e.g., after midline incision formation or with other interventions. As shown, the tissue matrix 10 could be positioned in various locations 170, 171, 172, 173, 174, corresponding to positions between various fascia layers. And, as noted previously, the device may be treated with the processes discussed herein on one or both sides. For example, a product positioned between two fascia or other tissue layers, such as those illustrated as 171, 172, 173, may be treated on both sides to prevent movement or space formation. Conversely, a device implanted in locations such as an intraperitoneal position (item 174) can be treated only on the side facing the peritoneum or abdominal wall and not on the side facing the abdominal viscera. Similar concepts would be considered for other abdominal locations or other locations within the body.

EXAMPLE 1

Figure 5A:
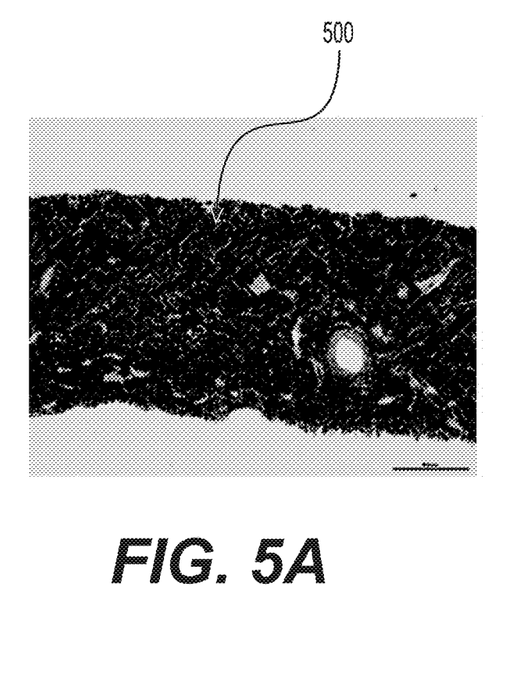
FIG. 5A illustrates a tissue matrix histologic section with Masson's trichrome staining prepared as described in Example 1.
Figure 5B:
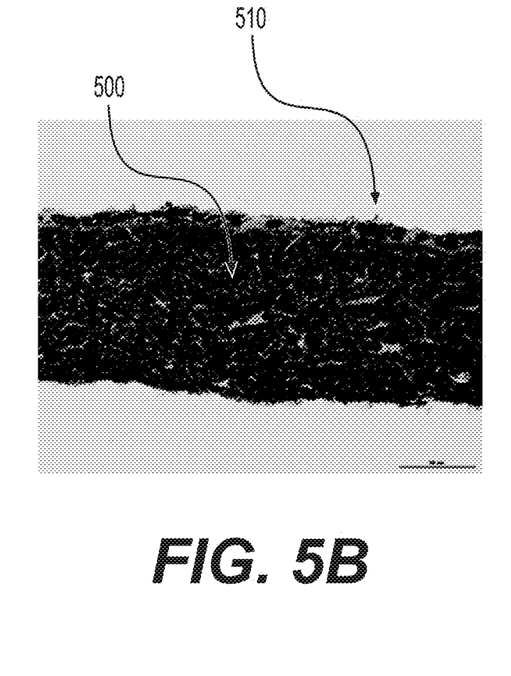
FIG. 5B illustrates a tissue matrix histologic section with Masson's trichrome staining prepared as described in Example 1 with a surface region having partially denatured collagen produced by laser treatment.

As discussed above, there are various ways available to partially denature collagen near the surface of a tissue matrix. As an example, the surface of an acellular porcine dermis was partially denatured following exposure to an EPILOG® Legend XL 120 $CO_2$ laser using a frequency of 5000 Hz at 60 W and a speed of 7.5 cm/s. The resulting tissue 500 was then processed for histological staining using Masson's Trichrome to evaluate the extent of collagen denaturation (FIG. 5B) as compared to non-treated acellular porcine dermis (FIG. 5A). As shown, laser treatment allows partial denaturation of collagen a finite distance from the surface of the matrix, thereby allowing formation of a denatured surface 510 in intimate contact with and connected to the underlying matrix.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:
1. A method of producing a tissue product, comprising:
selecting a first material comprising a collagen-containing tissue matrix;
treating a portion of the first material to partially denature collagen near a surface of the portion while leaving the remainder of the first material retaining a substantially intact collagen framework;

contacting the portion that has been treated to partially denature collagen with a composition comprising a transglutaminase enzyme; and placing the portion that has been contacted with the composition comprising transglutaminase in physical contact with a second material comprising a collagen-containing tissue matrix.

2. The method of claim 1, further comprising selecting at least one additional material comprising a collagen-containing tissue matrix;

treating a portion of the at least one additional material to partially denature collagen near a surface of the portion of the at least one additional material while leaving the remainder of the at least one additional material retaining a substantially intact collagen framework;

contacting the portion of the at least one additional material that has been treated to partially denature collagen with a composition comprising a transglutaminase enzyme; and placing the portion of the at least one additional material that has been contacted with the composition comprising transglutaminase in physical contact with the first material or second material.

3. The method of claim 1, wherein the composition comprising a transglutaminase enzyme comprises an aqueous solution.

4. The method of claim 1, wherein the first material and the second material comprise sponge formed from particulate.

5. The method of claim 1, wherein the first material and the second material are in the form of sheets.

6. The method of claim 1, wherein the first material and the second material are acellular tissue matrices.

7. The method of claim 6, wherein the acellular tissue matrices are produced from tissue derived from a tissue selected from skin, fascia, adipose, pericardial tissue, dura, umbilical cord tissue, placental tissue, cardiac valve tissue, ligament tissue, tendon tissue, arterial tissue, venous tissue, neural connective tissue, urinary bladder tissue, ureter tissue, and intestinal tissue.

8. The method of claim 6, wherein the acellular tissue matrices are produced from tissue derived from muscle.

9. The method of claim 1, wherein the first material and the second material each comprises a sheet of acellular tissue matrix, and the first material and the second material are contacted with one another to produce a multi-layer sheet.

10. The method of claim 9, wherein the multi-layered sheet comprises acellular muscle matrices.

11. A method of treatment, comprising:

selecting a material comprising a collagen-containing tissue matrix, wherein a portion of the material proximate a surface of the material includes partially denatured collagen while leaving the remainder of the material retaining a substantially intact collagen framework;

contacting the portion including partially denatured collagen with a composition comprising a transglutaminase enzyme; and placing the portion that has been contacted with the composition comprising transglutaminase in physical contact with a tissue site.

12. The method of claim 11, wherein the composition comprising a transglutaminase enzyme comprises an aqueous solution.

13. The method of claim 11, wherein the material comprising collagen-containing tissue matrix is in the form of a sheet.

14. The method of claim 11, wherein the material comprising collagen-containing tissue matrix comprises acellular tissue matrix.

15. The method of claim 14, wherein the collagen-containing tissue matrix is produced from tissue derived from a tissue selected from skin, fascia, adipose, pericardial tissue, dura, umbilical cord tissue, placental tissue, cardiac valve tissue, ligament tissue, tendon tissue, arterial tissue, venous tissue, neural connective tissue, urinary bladder tissue, ureter tissue, and intestinal tissue.

16. The method of claim 14, wherein the collagen-containing tissue matrix is produced from tissue derived from muscle.

17. The method of claim 11, wherein the steps of contacting the portion including partially denatured collagen with a composition comprising a transglutaminase enzyme and placing the portion that has been contacted with the composition comprising transglutaminase in physical contact with a tissue site are performed by contacting the tissue site with the transglutaminase and placing the surface of the material that includes partially denatured collagen in contact with the tissue site.

* * * * *